United States Patent [19]

McDonald

[11] 3,988,209

[45] Oct. 26, 1976

[54] MICROORGANISM ANALYSIS DEVICE

[76] Inventor: Bernard McDonald, 24826 Malibu Road, Malibu, Calif. 90265

[22] Filed: Apr. 17, 1975

[21] Appl. No.: 569,058

Related U.S. Application Data

[62] Division of Ser. No. 363,383, May 24, 1973, Pat. No. 3,894,845.

[52] U.S. Cl. .......................... 195/139; 195/103.5 R
[51] Int. Cl.² ........................................ C12K 1/04
[58] Field of Search ................. 195/120, 127, 103.5, 195/139; 23/253 R, 259, 230 B; 128/2 F, 272

[56] References Cited
UNITED STATES PATENTS

| | | | |
|---|---|---|---|
| 3,272,719 | 9/1966 | Avakian | 195/139 |
| 3,722,503 | 3/1973 | Hoviek | 128/2 F |

*Primary Examiner*—A. Louis Monacell
*Assistant Examiner*—R. B. Penland
*Attorney, Agent, or Firm*—Christie, Parker & Hale

[57] ABSTRACT

A device useful in medical laboratories for receiving urine and performing analyses thereof is described. In a preferred embodiment urine flows into portions on either side of a unitary housing. The two side portions are interconnected by an overflow reservoir. Urine first fills a plurality of upper compartments having preselected volume and then overflows a weir into the reservoir. In the other side portion a trough receives urine and wicks transfer a limited quantity thereof to nutrient media. A sample tube in the second side portion collects urine for sedimentation analysis. Excess urine overflows to the reservoir. A float in the reservoir closes off the weirs when the reservoir is filled. An inner housing within the side portion with nutrient media is removable for incubation.

In another embodiment the patient urinates into a receiving vessel having side apertures near its bottom and mounted on a float. Initially the urine flows from one aperture to a region beneath the float. After the float rises to a certain extent, the first aperture is occulted and urine overflows through a second aperture into a sample chamber. Thus, a midstream sample is obtained in the sample chamber.

11 Claims, 6 Drawing Figures

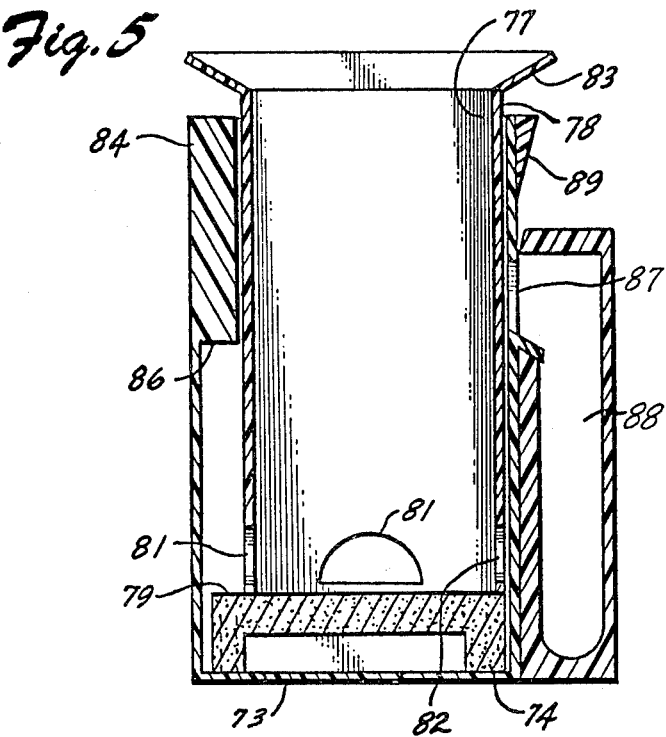
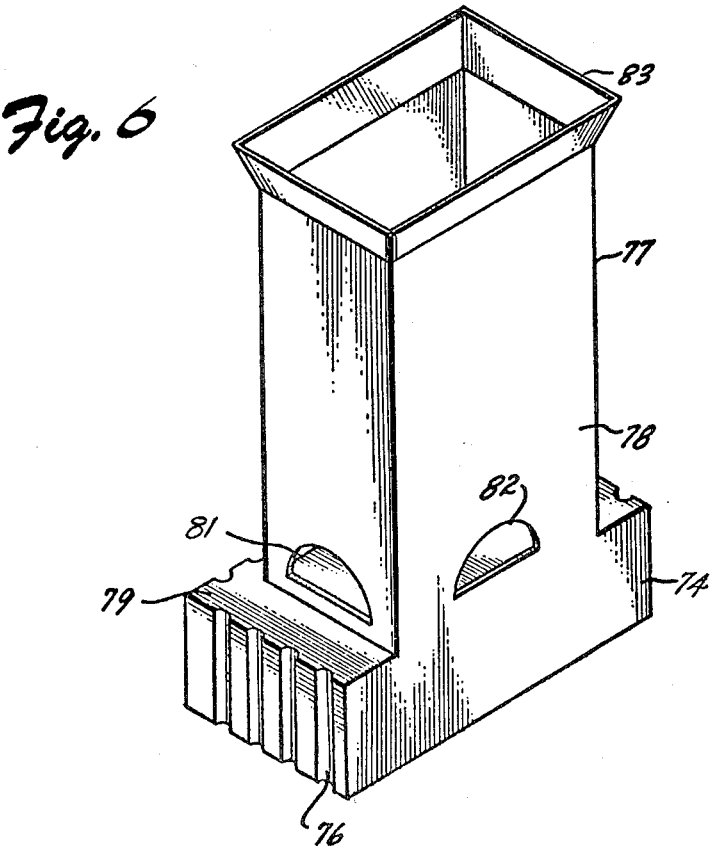

MICROORGANISM ANALYSIS DEVICE

CROSS-REFERENCE TO RELATED APPLICATIONS

This application is a division of copending patent application Ser. No. 363,383, filed May 24, 1973, issued as U.S. Pat. Ser. No. 3,894,845.

BACKGROUND OF THE INVENTION

Analysis of urine is one of the most commonly used medical techniques since the chemistry of a patient's urine reflects so may physiological conditions. The techniques for collection and analysis are archaic to say the least. The usual technique is to have the patient provide a urine sample in a bottle or cup and this vessel is delivered to the laboratory. Open cups or bottles are susceptible to spillage and it is surprising how inept people are in placing caps on bottles.

When the sample reaches the laboratory it may sit around for some time before the technician gets around to performing the required analysis. For many chemical tests this is of no great concern since the urine does not change rapidly. When tests are to be made for microorganisms, however, it is desirable to commence culture growth promptly so that the viability of organism is assured. It is impossible to say how many culture tests are reported negative simply because the technicians have unduly delayed the commencement of growth.

It is therefore desirable to provide a technique for obtaining urine samples with minimum chance for spillage between collection and the laboratory and where tests can be performed quickly and accurately with minimum time and mess.

For some tests, particularly for microorganism culture, it is desirable to obtain what is known as a midstream sample. The initial flow of urine may be contaminated with microorganisms from the external urethra and the initial portion of the stream is discarded. After this flushing action the balance of the stream may be collected for analysis. Previously this has been accomplished by having the patient urinate into more than one container or simply discard the first part of the stream and then urinate into the sample container. In children and elderly patients, such a technique is often unsatisfactory.

BRIEF SUMMARY OF THE INVENTION

There is, therefore, provided in practice of this invention according to a presently preferred embodiment, a laboratory device in the form of a housing having a collection compartment and a plurality of sample compartments in the housing at least some of which contain microorganism nutrient. Urine is directed into the collection compartment and overflows into a reservoir when the compartment is filled. Wicks also lead to the compartments with nutrient for microorganism culture. This portion can be removed and placed in a controlled temperature oven as soon as received in the laboratory.

DRAWINGS

These and other features and advantages of the present invention will be appreciated as the same becomes better understood by reference to the following detailed description when considered in connection with the accompanying drawings wherein:

FIG. 5 is a transverse cross section through a urine collection and analysis device particularly suited for obtaining a midstream sample; and FIG. 6 illustrates a float and receiving vessel for the device of FIG. 5.

DESCRIPTION

Figure 1:
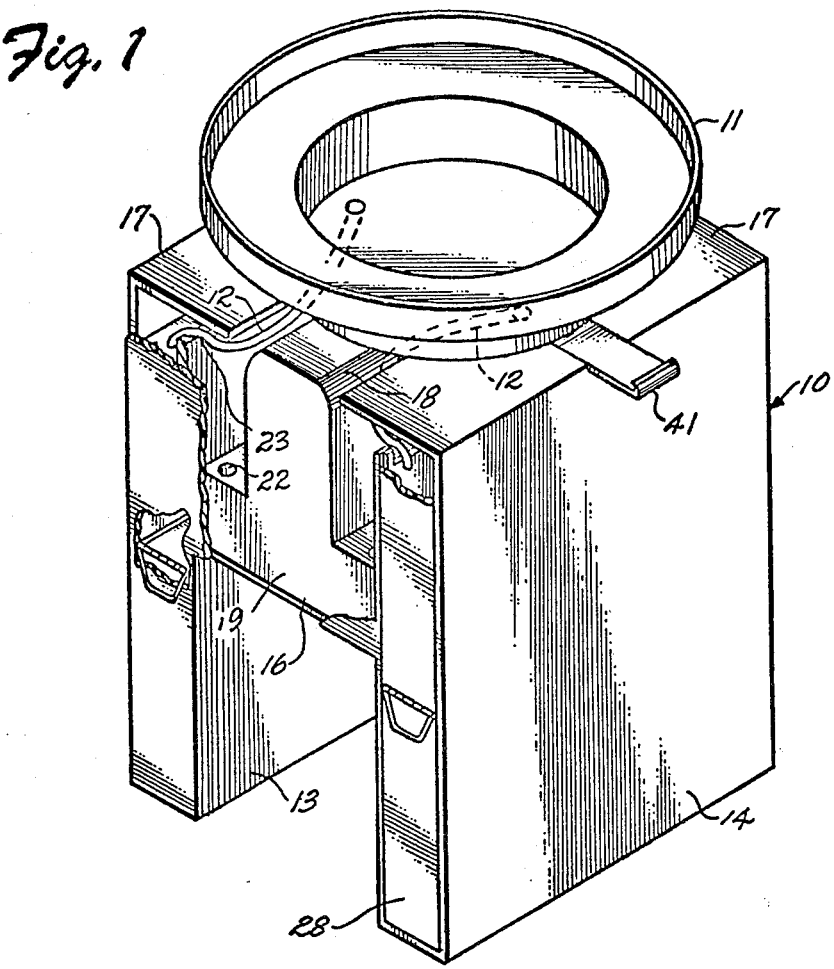
FIG. 1 illustrates in perspective a urine collection and analysis device constructed according to principles of this invention.

In the illustration of a presently preferred embodiment shown in perspective in FIG. 1 a portion has been cut away to show some of the interior. This laboratory device for urine collection and analysis comprises a plastic housing 10 on top of which a shallow pan 11 is placed. The pan 11 is formed of thin plastic or water resistant treated paper and is sufficiently flexible that it can be safely flushed down a toilet if desired. Flexible tubes 12 lead from the bottom portion of the pan into the interior of the housing 10.

Figure 2:
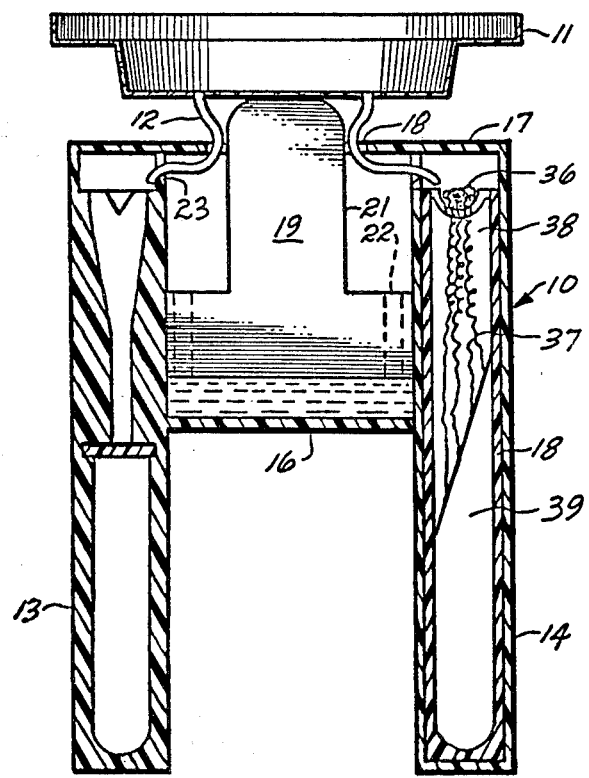
FIG. 2 is a transverse cross section of the device.
Figure 4:
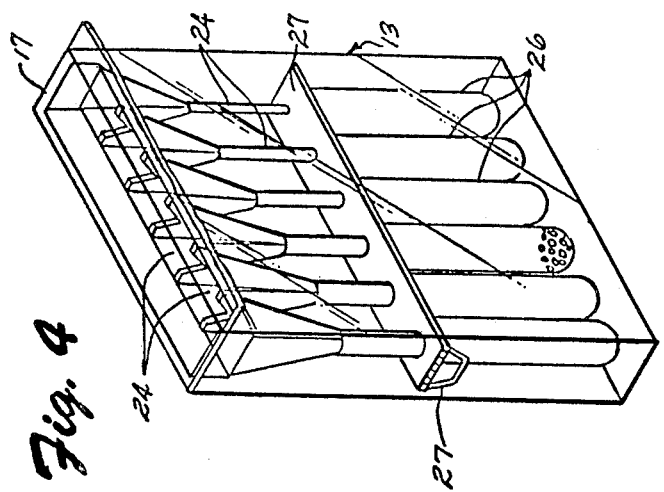
FIG. 4 illustrates a portion of the device having sample collection and analysis compartments.

The housing has a generally U-shape in transverse cross section as is also seen in FIG. 2. The device has two depending side portions 13 and 14 interconnected by an overflow reservoir 16. One of the side portions 13 is also illustrated in FIG. 4 as if it were a separate article; that is the reservoir portion 16 and other side portion 14 have been removed for purposes of illustration. The top portion of the housing 10 is partly closed by horizontally extending sheets 17 extending part way inwardly from each edge to leave a longitudinal slot 18 across the top of the device. A T-shaped float 19 of very lightweight material, such as polystrene foam fits in the central overflow reservoir with the upstanding leg 21 of the float 19 fitting through the slot 18 in the top of the device. Since the float fits rather closely within the reservoir, holes 22 are provided through the crossbar of the T so that urine can flow therethrough. The pan 11 is on top of the leg 21 of the float and is preferably lightly secured thereto by an adhesive to keep it from being accidently dislodged, but still removable when desired.

The interior of side portion 13 is open along its length below the top sheet 17 so that urine can flow to any portion. An overflow weir or slot 23 communicates between the side portion 13 and the central reservoir 16. When the pan 11 is in place one of the tubes 12 extends over the weir 23 and into the side portion so that urine flows directly thereto from the pan.

The side portion 13 of the housing is subdivided into a plurality of funnel-shaped upper compartments 24. It will be noted in FIG. 4 that the volumes of the several compartments may be different so that the volume of fluid contained in each differs. The tops of the several compartments 24 are below the height of the weir 23 so that when urine flows into the side portion 13 it flows into the several upper compartments 24 until all are filled before it overflows the weir into the central reservoir.

The side portion 13 also has a plurality of lower compartment 26 in one to one correlation with the upper compartments 24. A removable slide 27 temporarily seals the lower compartments from the respective upper compartments. Each of the lower compartments 26 contains a suitable reagent (not shown) preferably in dry form for performing a urine analysis, such as for example, for the presence of blood in the urine, pH, ketone content, density, or the like.

Figure 3:
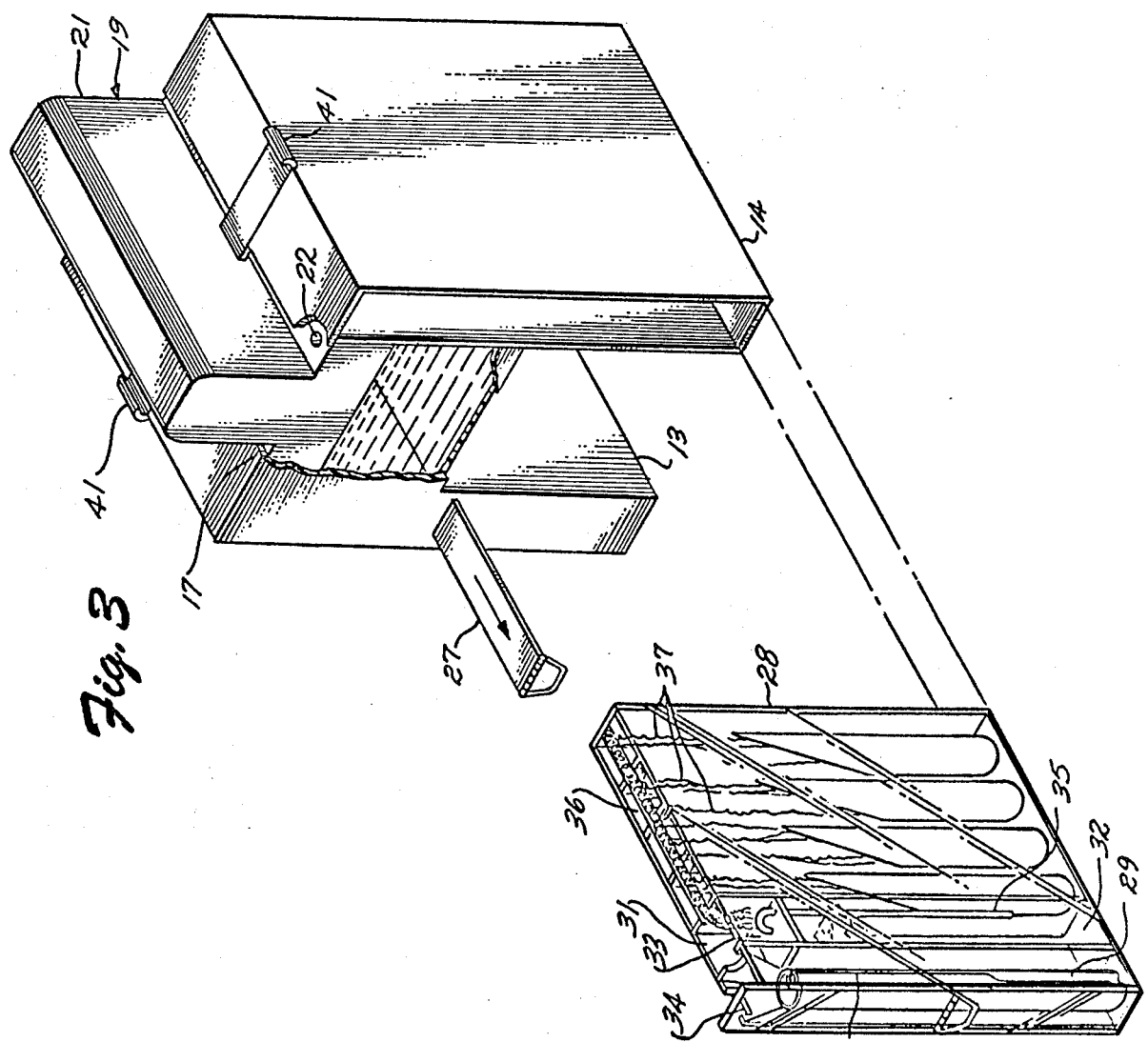
FIG. 3 is a partial cutaway view of the device when filled with a removable portion having means for growing organism cultures exploded therefrom.

When the device is used urine collects in the upper compartments 24 in a predetermined volume. When the laboratory technician is ready to perform an analysis, the slide 27 is removed as illustrated in FIG. 3, which permits the urine in the upper compartments 24 to flow down into the lower compartments 26 where the analysis reagents are stored. The differing volumes of the upper compartments 24 provides a suitable volume for the analysis performed in the respective lower compartment.

The other side portion 14 of the laboratory device has a removable inner housing or cassette 28 which can be withdrawn after urine is collected as illustrated in FIG. 3. This inner housing 28 also has a plurality of compartments which are in fluid communication with each other at their upper portion. In the first compartment adjacent an overflow weir 34 there is a removable sedimentation tube 29. The second compartment in the inner housing 28 has an upper portion 31 and a lower portion 32 separated by a rigid membrane 33. A capillary siphon 35 extends between the upper compartment 31 and lower compartment 32 for transferring a small amount of urine therebetween. The lower compartment 32 is partly filled with sterile nutrient broth for growing microorganisms and the capillary siphon transfers a proper quantity of urine from the upper compartment to the lower compartment to fill the space over the nutrient broth and innoculate the broth for microorganism growth. Use of a capillary siphon prevents spillage of the broth before the device is used.

The balance of the compartments in the side portion 14 have a shallow trough over their top with a height above that of the weir 34 leading from the first compartment into the central reservoir. A permeable wick 36 lies in the trough and has an end in the upper compartment 31. Permeable threads 37 from the wick extend down into the additional compartments 38 of the side portion. Each of these compartments 38 has a solid nutrient medium 39 such as a conventional agar slant for growth of microorganisms. On such a solid nutrient substrate the small quantity of urine required for innoculation, is delivered by the threads 37 of the wick 36.

Thus when the device is used urine flows into the side portion 14, filling the sedimentation tube 29 and upper compartment 31 before overflowing the weir 34 into the central reservoir 16. A small portion of the urine is transferred to the agar slants 39 in the several compartments 38 by the wick 36 and a limited quantity is transferred to the lower compartment 32 by way of the capillary siphon 35. When the side portion 14 is thus filled, the inner housing 28 is removed for use in the laboratory. The sedimentation tube 29 is removed and the balance of the inner housing is placed in an incubation oven at 37° C for optimum growth of microorganisms. By using several nutrient media in the agar slants selectivity of growth of microorganisms can be obtained so that several cultures can be made simultaneously. It will be noted that the nutrient media is automatically innoculated in the collection device and the only handling by the technician is to remove the sedimentation tube 29 and place the inner housing 28 in the incubation oven.

The laboratory device serves for collection of urine as well as analysis. Urine is received in the pan 11 and flows through the tubes 12 into the side portions 13 and 14 of the housing. When these respective side portions fill, excess urine overflows the weirs 23 and 34 into the central overflow reservoir 16. This causes the float 19 to rise, gradually lifting the pan and withdrawing the tubes 12 from the filled side portions and permitting flow directly into the reservoir until it is filled. At this time the pan is simply pulled off and discarded. The float rises against the upper sheets 17 thereby closing off the holes 22 through the float. The sides of the float also close off the weirs 23 and 34. A pair of slides 41 are mounted in dovetail slots in the top portion of the device so that when the float has reached its upper extent, the slides can be pinched together to penetrate the sides of the polystyrene foam float and lock it in its uppermost position thereby inhibiting spillage of urine from the reservoir as the device is taken to the laboratory.

In the laboratory, the technician removes the slide 27 from the side portion 13 and observes color changes in the lower compartments 26 for almost instant analysis of the urine. The inner housing 28 is removed from the other side portion 14 and the sedimentation tube lifted out. Thereupon the balance of the inner housing is placed in the incubation oven for conventional growth of microorganisms. Since no transfer of urine from the collection device is required in the laboratory, the analyses can be performed very promptly and economically. It will also be noted that innoculation of the nutrient media occurs while the urine is still fresh, significantly reducing mortality of microorganisms. Further, the steps needed in the laboratory are minimal and the cultures are usually transferred to the incubation chamber much more promptly than with prior laboratory techniques. The excess quantity of urine in the reservoir 16 is ordinarily simply discarded with the device after analyses have been performed. It is available however in case specialized tests are required. A small amount of preservative for the urine may be provided in the reservoir when the unit is built.

FIG. 5 illustrates in vertical cross-section another embodiment of urine collection and analysis device particularly suitable for obtaining a midstream sample. In this device, the first portion of the urine stream which may contain contaminating microorganisms from the urethra is diverted into one compartment and the following portion of the stream is collected as the sample to be analyzed.

The midstream sampling device has a rectangular plastic container 73 opened at its upper end and a special float is mounted within the container. The float has a buoyant porous plastic base 74 which, as better seen in the perspective view of the float in FIG. 6, has flutes or scallops 76 on its sides for letting urine pass. An open top receiving vessel or receptacle is mounted on the buoyant base 74 in a manner such that one face 78 of the combined receptacle and float is flat. The receiving vessel is set back from the other three faces of the float to form an upwardly facing shoulder 79 around three sides. Openings 81 are provided in three faces of the vessel above the shoulder 79. A fourth opening 82 is provided through the wall of the vessel at its lower end on the flat face 78. A flared lip 83 is provided at the upper open end of the vessel. If desired, the float may be a chamber with closed top and open bottom to obtain buoyancy from a trapped bubble of air.

The collection container has an internally enlarged portion 84 near its upper portion on three sides, forming a downwardly facing shoulder 86 opposed to the upwardly facing shoulder 79 on the float. The fourth side of the collection compartment opposite the flat face 78 of the combined vessel and float is also flat so that there is a relatively close fit therebetween. A passage 87 is provided through the wall of the compartment 73 on this face so that urine may flow from the collection container into a sample compartment 88 on one side thereof. The sample compartment 88 is indicated in FIG. 5 only as an open receptacle, however, it will be understood that this may be a microorganism module similar to the removable cassette-like module 28 hereinabove described and illustrated. If desired, the sample chamber 88 can simply be detached for recovering the urine therein for analysis. A cutter 89 is mounted on the collection vessel 73 in a dovetail groove (not shown) for severing the sample container 88 and prying it away from the collection compartment. The urine therein can then be handled in the usual manner.

To use the sample collection device illustrated in FIG. 5 the patient urinates into the open upper end of the receiving vessel 77 and the urine passes through the apertures 81 and over the flutes 76 to collect in the region of the collection compartment beneath the float 74. Since the opening 82 is in close proximity to the wall of the container 73, only a small amount of urine flows therethrough. Urine from a first part of the stream therefore collects beneath the float and causes it to be buoyed upwardly. This continues until the shoulder 79 on the float engages the shoulder 86 within the collection chamber. At this point, the apertures 81 are rather close to and occulted by the enlarged portion 84 within the container and little, if any, urine flows therethrough. The opening 82 on the flat face 78 of the float has now been elevated to a point opposite the passage 87 into the sample compartment 88 and most of the urine, which is free of any contamination of the first portion of the stream flows into the sample chamber. Any excess of urine simply collects in the receiving vessel at an elevation above the opening 87.

After the sample has thus been obtained, the cutter 89 can be brought down, severing the sample chamber from the balance of the container. The cutter not only removes the sample chamber but also closes off the passage 87 thereby minimizing spillage of urine during sample removal. The collection container is then discarded and the urine in the sample chamber 88 is transferred to an incubation oven for microorganism analysis either by a subsequent transfer or by incubation directly in the sample chamber.

Although limited embodiments of urine collection and analysis device have been described and illustrated herein, many modifications and variations will be apparent to one skilled in the art. Thus, for example, instead of collecting urine directly from a patient in such devices, some embodiments may be used in the laboratory by decanting a specimen previously collected. This enables filling of several compartments substantially simultaneously so that numerous analyses and cultures can be commenced in a single operation rather than several distinct steps. Many other modifications and variations will be apparent to one skilled in the art and it is therefore to be understood that within the scope of the appended claims, the invention may be practiced otherwise than as specifically described.

What is claimed is:

1. A laboratory device for performing urinalysis comprising:
    a housing;
    a collection compartment in the housing for receiving urine;
    a plurality of separate test compartments in the housing isolated from the collection compartment so that urine cannot flow directly from the collection compartment to the test compartments;
    nutrient means in each test compartment for growth of microorganisms;
    wick means between the collection compartment and the respective test compartments for transferring a limited quantity of urine from the collection compartment to the nutrient means in the test compartments;
    an overflow reservoir for receiving urine in excess of the amount needed to fill the collection compartment and
    overflow means between the collection compartment and the reservoir for conducting urine to the overflow reservoir when a predetermined quantity has entered the collection compartment.

2. A laboratory device as defined in claim 1 wherein the test compartments are in a cassette removable from the housing for incubation.

3. A laboratory device as defined in claim 2 further comprising a culture compartment containing a liquid nutrient medium for growth of microorganisms and a capillary siphon in fluid communication between the collection compartment and the liquid nutrient medium.

4. A laboratory device for performing urinalysis comprising:
    means for collecting a midstream sample of urine in a collection compartment;
    a plurality of test compartments having nutrient means in each test compartment for growth of microorganisms; and
    means connecting the collection compartment to each of the test compartments including wick means extending between the collection compartment and the respective test compartments for transferring a limited quantity of urine from the collection compartments to the nutrient means by capillary action.

5. A laboratory device for urinalysis comprising:
    a housing;
    a collection compartment in the housing for receiving urine;
    means for receiving urine in the upper portion of the housing and directing flow into said collection compartment;
    an overflow reservoir for receiving urine in excess of the amount needed to fill said collection compartment;
    a plurality of test compartments in the housing having nutrient means in each test compartment for growth of microorganisms;
    wick means between the collection compartment and the respective test compartments for transferring a limited quantity of urine to the nutrient means from the collection compartment; and
    means between the collection compartment and the reservoir for conducting urine to the overflow reservoir when a predetermined quantity has entered the collection compartment.

6. A laboratory device as defined in claim 5 wherein the test compartments are in a cassette removable from the housing for incubation.

7. A laboratory device as defined in claim 6 further comprising a culture compartment containing a liquid nutrient medium for growth of microorganisms and a capillary siphon in fluid communication between the collection compartment and the liquid nutrient medium.

8. A laboratory device as defined in claim 6 further comprising:
a float in the reservoir; and
means on the float for closing said conducting means when the reservoir fills.

9. A laboratory device as defined in claim 8 wherein a portion of the float extends through a slot in the top of the device; and the means for receiving urine comprises a pan on the top of the float and a flexible tube extending from the pan into the collection compartment.

10. A laboratory device as defined in claim 5 wherein the housing has a generally U-shape with the overflow reservoir forming the bight of the U, and wherein the test compartments are in a row in one of the legs of the U.

11. A laboratory device for body fluid analysis comprising:
a sample receiving compartment;
a test compartment having a microorganism nutrient medium therein;
and capillary tube siphon means between the sample receiving compartment and the test compartment for conveying a small amount of body fluid to the test compartment.

* * * * *